United States Patent [19]

Grollier

[11] Patent Number: 4,935,032

[45] Date of Patent: Jun. 19, 1990

[54] METHOD FOR HOT DYEING HAIR WITH COMPOSITIONS WHICH ARE SUPERSATURATED WHEN COLD

[75] Inventor: Jean F. Grollier, Paris, France

[73] Assignee: L'Oreal, Paris, France

[21] Appl. No.: 750,273

[22] Filed: Jul. 1, 1985

[30] Foreign Application Priority Data

Jul. 5, 1984 [LU] Luxembourg ............ 85450

[51] Int. Cl.⁵ .................................. A61K 7/13
[52] U.S. Cl. ............................. 8/414; 8/405; 8/406; 8/428
[58] Field of Search ............. 8/405, 406, 414, 428

[56] References Cited

U.S. PATENT DOCUMENTS

| | | | |
|---|---|---|---|
| 3,168,442 | 2/1965 | Brunner et al. | 8/405 |
| 3,733,175 | 5/1973 | Alperin et al. | 8/405 |
| 4,470,826 | 9/1984 | Bugaut et al. | 8/406 |

FOREIGN PATENT DOCUMENTS

| | | | |
|---|---|---|---|
| 2317140 | 10/1974 | Fed. Rep. of Germany | 8/405 |
| 2207690 | 6/1975 | France | 8/405 |

*Primary Examiner*—Douglas W. Robinson
*Attorney, Agent, or Firm*—Cushman, Darby & Cushman

[57] ABSTRACT

Method for dyeing human hair, comprising the steps of applying to hair a composition the temperature of which is higher than 30° C. and lower than 50° C. and which contains at least one nitro dyestuff of the benzene series supersaturated relative to its solubility limit at ambient temperature in a cosmetic medium suitable for dyeing hair and chosen from the dyestuffs having a ratio KC lim greater than 2 is aqueous solution, KC lim being the ratio of the limiting concentrations of the dyestuff in an aqueous medium which are measured at 50° C. and 18° C.; maintaining this composition in contact with hair either at ambient temperature or at a temperature above room temperature and below 50° C., and rinsing the hair.

9 Claims, No Drawings

METHOD FOR HOT DYEING HAIR WITH COMPOSITIONS WHICH ARE SUPERSATURATED WHEN COLD

The present invention relates to a new method for dyeing hair employing solutions of direct dyestuffs.

It is well known in the field of hair dyeing that various classes of dyestuffs may be employed.

Among these, the most effective class is that of oxidative dyestuffs which makes it possible to produce shades of varied intensity and tints. It is possible, especially, to produce shades of natural appearance which are very dark by virtue of phenomena of oxidative condensations within the hair.

Use is made, furthermore, of dyestuffs known as direct, which dye hair in the absence of an oxidation process. This range of dyestuffs includes the direct nitro dyestuffs of the benzene series, which are capable of penetrating within the hair and which consequently give shades which are fairly resistant to washing without, however, attaining the very high tenacity of the oxidative dyestuffs.

The nitro dyestuffs of the benzene series also present the problem of a relative lack of intensity, particularly in the area of blue and yellow dyestuffs, which are used to develop natural shades. The affinity of these dyestuffs is frequently good for hair sensitized by a permanent-wave, but is weaker for natural hair, resulting in the dyes being selective.

In practice, such dyestuffs do not make it possible to produce shades which are as dark as those produced with oxidative dyestuffs under their normal use conditions.

To overcome this disadvantage it has already been proposed to carry out direct dyeing with nitro colorants of the benzene series under a cap or under a drier hood in order to maintain a higher temperature in the region of the hairy skin.

Since the temperature promotes diffusion phenomena, a slight gain in tinctorial power is produced, but which still does not wholly satisfy the requirements of hair-dyeing specialists.

The Applicant has found that the temperature increase was capable of having an effect not only on the range of application of the dyestuffs to hair but also on the tinctorial composition itself. The applicant has found, in particular, that in the case of some direct nitro dyestuffs the temperature increase made it possible to increase greatly the concentrations of the dissolved dyestuffs, but without these increases in the quantities of dissolved dyestuffs resulting, as might be expected, in a levelling off of the coloration owing to a saturation phenomenon. In particular, a spectacular gain in tinctorial power is observed.

This process makes it possible to produce extremely powerful shades with an intensity which is substantially equal to that which can be produced with oxidative colorants, this being the case even for hair which has not been sensitized by a permanent-wave. Furthermore, the dyes have good resistance to light, washing and to inclement weather, and a clear decrease in the selectivity of these colorants towards hair is observed as a very clear improvement in the uptake on unsensitized hair and good covering of white hair.

The subject of the invention is consequently a dyeing process employing direct nitro dyestuffs of the benzene series present in dye compositions at concentrations which are greater than their solubility limit at ambient temperature in the cosmetic media employed.

Ambient temperature is understood to mean the range of temperatures between 15° and 25° C., which represents the range of temperatures in premises where hair coloring products are usually applied.

Other subjects of the invention will be revealed on reading the description of the examples which follow.

The hair-dyeing process according to the invention is substantially characterised by the application to hair of a composition containing, in a cosmetic medium which is suitable for dyeing, at least one nitro dyestuff of the benzene series, of formula:

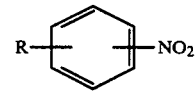

in which R denotes an amino group or an amino group mono- or disubstituted by an alkyl or hydroxyalkyl group, the aromatic nucleus being furthermore capable of carrying one or more other substituents chosen from alkyl, alkoxy, hydroxyalkoxy, halogen or amino groups, or amino groups mono- or disubstituted by an alkyl or hydroxyalkyl group, this or these colorant(s) having a value of KC lim greater than 2 in aqueous medium; KC lim is defined as the ratio $$KC\ Lim = \frac{C\ Lim\ 50}{C\ Lim\ 18}$$

C lim 50 being the limiting concentration at 50° C. and C lim 18 being the limiting concentration at 18° C., this or these colorant(s) being present in the dye composition supersaturated relative to their solubility limit at ambient temperature, the composition at the time of use being at a temperature between 30° C. and 50° C. which is sufficient to solubilize all of the dyestuffs and compatible with contact with the hairy skin. The application of the dye composition is followed by an exposure to ambient temperature or to a temperature higher than ambient temperature and lower than 50° C.

The value of KC lim is determined by dissolving the dyestuff in question in water containing 10% of ethyl cellosolve and adjusted to pH=9.6 for a temperature change from 18° to 50° C. The limiting concentrations of the colorant are determined at 18° C. and 50° C.

The dyestuff which has a KC lim value greater than 2 for a temperature change from 18° to 50° C. meets the criteria of the invention.

The Applicant has found that the choice of these dyestuff results, surprisingly, in a spectacular gain in tinctorial power.

The dye compositions according to the invention are heated to the required temperature by virtue of a suitable device such as a heating mantle, a hotplate, a thermostat bath or a microwave oven.

The concentration of dyestuffs according to the invention is preferably such that at ambient temperature at least 0.05% of a dyestuff defined as above is in an undissolved state in the composition.

The supersaturated colorants dissolve gradually, the dissolution taking place over a period of a few seconds to several minutes, depending on the nature of the medium.

The composition is applied to hair at a temperature higher than 30° C. and lower than 50° C.

According to a first alternative form, the hot dye composition containing the dyestuffs is applied to hair and the hair is maintained at a temperature above ambient temperature by using a heating drier hood or cap.

According to another alternative form, the dye composition is applied in ambient air and, depending on the kinetics of cooling and the initial supersaturation state, the colorant will or will not precipitate on hair. To this end, the concentration of colorants is adjusted, for reasons of quality of the results and of economy of the coloring materials, in order that at the end of the exposure time there should be no supersaturation as a function of the final temperature attained.

After the exposure time the hair is then rinsed in a conventional manner and one or more shampoos are, or are not, applied.

The exposure times will be optionally capable of being shortened relative to the conventional compositions containing the same dyestuffs but in different proportions. These exposure times can very between 5 and 30 minutes.

The dyestuffs which are more particularly capable of being employed in the compositions and in the process according to the invention are chosen especially from:

2-N-β-hydroxyethylamino-5-N,N-bis-β-hydroxyethylaminonitrobenzene (KC lim=6.2)

2-N-methylamino-5-N,N-bis-β-hydroxyethylaminonitrobenzene (KC lim=3.2)

2-N-methylamino-5-N-methyl-N-β-hydroxyethylaminonitrobenzene (KC lim=6.5)

2-N-β-hydroxyethylamino-5-N-methyl-N-β-hydroxyethylaminonitrobenzene (KC lim=6.2)

2-N-methylamino-4-β-hydroxyethoxynitrobenzene (KC lim=3.0)

2-N-β-hydroxyethylaminonitrobenzene (KC lim=3.2)

3-β-hydroxyethoxy-4-N-β-hydroxyethylaminonitrobenzene (KC lim=6.8)

3-methoxy-4-N-β-hydroxyethylaminonitrobenzene (KC lim=4.0)

2-N-β-hydroxyethylamino-5-aminonitrobenzene (KC lim=2.7)

2-amino-5-N-β-hydroxyethylaminonitrobenzene (KC lim=6.6)

3,4-diaminonitrobenzene (KC lim>5.0)

3-amino-4-N-β-hydroxyethylaminonitrobenzene (KC lim=2.5)

2-amino-5-N-methylaminonitrobenzene (KC lim=2.4)

3,4-bis-N-β-hydroxyethylaminonitrobenzene (KC lim=5.0)

3-amino-4-hydroxynitrobenzene (KC lim=5.3)

2,5-N-β-hydroxyethylaminonitrobenzene (KC lim=11.9)

2-hydroxy-5-aminonitrobenzene (KC lim=13.1)

3-hydroxy-4-aminonitrobenzene (KC lim=3.6)

2-amino-5-hydroxynitrobenzene (KC lim=2.4)

2-N-β-hydroxyethylamino-5-hydroxynitrobenzene (KC lim=5.4)

2-amino-3-hydroxynitrobenzene (KC lim=9)

3-hydroxy-4-N-β-hydroxyethylaminonitrobenzene (KC lim=6.8).

The compositions may naturally contain other nitro colorants which do not meet this condition.

The total proportion of the dyestuffs employed in the dye compositions is between 0.2 and 20% and preferably between 0.5 and 10% by weight.

The compositions which may be employed according to the invention can be in various forms such as in the form of more or less thickened solutions.

They may contain cosmetic ingredients usually employed in a composition of this type, and particularly anion, cationic, nonionic, or amphoteric surface-active agents or their mixtures.

Among these surface-active agents, particular mention may be made of alkylbenzenesulphonates and alkylnaphthalenesulphonates, fatty alcohol sulphates, ethersulphates or sulphonates, fatty acid quaternary ammonium salts or diethanolamides, polyoxyethylenated and polyglycerolated acids, amides, amines or alcohols, and polyoxyethylenated and polyglycerolated alkylphenols.

These surface-active products are present in the compositions according to the invention in proportions of between 0.5% and 55% by weight and preferably between 4 and 40% by weight relative to the total weight of the composition.

The compositions according to the invention may also contain organic solvents, provided, however, that these solvents do not have a boiling point which is too low and a vapor pressure which is too high at 50° C. In particular, the use of ethanol, isopropanol and tert-butanol should be avoided.

Among the organic solvents which can be employed in the compositions according to the invention, mention may be made of glycerol, 1-propanol, $C_4$ and $C_5$ alkanols other than tert-butanol, phenylethanol, benzyl alcohol, propylene glycol, diethylene glycol, triethylene glycol, tetraethylene glycol, butylene glycol, glycol alkyl or aryl ethers such as propylene glycol methyl ether, dipropylene glycol methyl ether, tripropylene glycol methyl ether, ethylene glycol methyl ether, ethylene glycol ethyl ether, ethylene glycol butyl ether, diethylene glycol methyl ether, diethylene glycol ethyl ether, diethylene glycol butyl ether, ethylene glycol phenyl ether, diethylene glycol isobutyl ether, diethylene glycol hexyl ether, trimethylene glycol ethyl ether, trimethylene glycol butyl ether, 1-butoxy-2-propanol, ethylene glycol diethyl ether, ethylene glycol dibutyl ether, ethylene glycol monobenzyl ether, diethylene glycol dimethyl ether, diethylene glycol diethyl ether, diethylene glycol dibutyl ether, triethylene glycol dimethyl ether, tetraethylene glycol dimethyl ether and 1,3-butylene glycol methyl ether, these solvents being capable of being employed alone or as mixtures.

The solvents are preferably present in proportions ranging from 1 to 40% by weight, and more particularly from 2 to 30% by weight relative to the total weight of the composition.

The compositions according to the invention may be thickened preferably with compounds chosen from sodium alginate, gum arabic, cellulose derivatives such as methyl cellulose, hydroxyethyl cellulose, hydroxypropyl ethyl cellulose and carboxymethyl cellulose, and various polymers which function in this way, such as, in particular, acrylic acid derivatives.

It is also possible to employ inorganic thickeners such as bentonite.

The thickeners are preferably present in proportions of between 0.5 and 5% by weight and, in particular between 0.5 and 3% by weight relative to the total weight of the composition.

It is also possible to add to the compositions according to the invention any other adjuvant usually employed in hair-dyeing compositions and, in particular, penetrating agents, sequestering agents, film-forming agents and perfumes. The pH of the dye compositions employed within the scope of the invention may be between 3 and 11 and, preferably, between 5 and 10, and will be adjusted with acids or bases of an inorganic or organic origin.

The following examples are intended to illustrate the invention without being of a restrictive nature.

EXAMPLE 1

| | |
|---|---|
| 2-N-β-Hydroxyethylamino-5-N,N-bis-β-hydroxyethylaminonitrobenzene | 4.4 g |
| 2-N-Methylamino-4-β,γ-dihydroxypropoxynitrobenzene | 1.5 g |
| 2-N-methylamino-5-N,N-bis-β-hydroxyethylaminonitrobenzene | 0.9 g |
| Lauric acid | 1.0 g |
| Oleyldiethanolamide | 3.0 g |
| Butyl glycol | 5.0 g |
| Ethomeen HT 60 sold by Akzo | 3.5 g |
| Natrosol 250 HHR sold by Hercules (hydroxyethyl cellulose) | 0.25 g |
| 2-Amino-2-methyl-1-propanol q.s. pH = 9.5 | |
| Demineralized water q.s. | 100.0 g |

This composition is heated to a temperature of 45° C. before application. After 15 minutes' stirring at this temperature, the composition is applied to light-brown hair containing a fairly high percentage of white hair. It is left exposed for 25 minutes under a drier hood at 45° C.

The hair is rinsed, shampooed and dried.

The hair is then dyed black. Uniformity is very good and white hair is covered.

EXAMPLE 2

| | |
|---|---|
| 2-N-βhydroxyethylamino-5-aminonitrobenzene | 0.5 g |
| 3,4-N-bis-β-hydroxyethylaminonitrobenzene | 0.15 g |
| 2-N-β-Hydroxyethylamino-5-hydroxynitrobenzene | 0.7 g |
| 2-N-β-hydroxyethylamino-5-β,γ,-dihydroxypropoxynitrobenzene | 0.5 g |
| Lauric acid | 1.0 g |
| Oleyldiethanolamide | 3.0 g |
| Butyl glycol | 5.0 g |
| Ethomeen HT 60 sold by Akzo | 3.5 g |
| Natrosol 250 HHR sold by Hercules | 0.25 g |
| 2-Amino-2-methyl-1-propanol q.s. pH = 9.5 | |
| Demineralized water q.s. | 100.0 g |

This liquid composition is heated to a temperature of 45° C. and after dissolving is applied to brown hair. It is left exposed for 25 minutes. It is rinsed off and a shampoo is applied. The hair is then uniformly colored with an intense auburn tint.

| | |
|---|---|
| 2-Amino-5-N-β-hydroxyethylaminonitrobenzene | 1.0 g |
| 2-N-β-hydroxyethylamino-5-aminonitrobenzene | 0.4 g |
| 2-N-Methylamino-5-N-methyl-N-β-hydroxyethylaminonitrobenzene | 0.3 g |
| 2-N-β-Hydroxyethylamino-5-hydroxynitrobenzene | 0.4 g |
| Lauric acid | 1.0 g |
| Oleyldiethanolamide | 3.0 g |
| Butyl glycol | 5.0 g |
| Ethomeen HT 60 sold by Akzo | 3.5 g |
| Natrosol 250 HHR sold by Hercules | 0.25 g |
| 2-Amino-2-methyl-1-propanol q.s. pH = 9.5 | |
| Demineralized water q.s. | 100.0 g |

The thickened liquid is preheated to 45° C. before use and applied to dark brown hair for 25 minutes. After rinsing and shampooing, an intense, very uniform, purple-violet tint is produced on the hair.

We claim:

1. In a method for dyeing human hair with a hair dye composition comprising in an aqueous medium 0.2 to 20 weight percent of a nitrobenzene dye, the improvement comprising selecting as said nitrobenzene dye one having a value of KC lim greater than 2 in an aqueous medium, said KC lim being defined as the ratio $$KC\ \text{lim} = \frac{C\ \text{lim}\ 50}{C\ \text{lim}\ 18},$$

C lim 50 being the limiting concentration of said nitrobenzene dye at 50° C. and C lim 18 being the limiting concentration of said nitrobenzene dye at 18° C., in an aqueous medium, said nitrobenzene dye being present in said hair dye composition supersaturated relative to its solubility limit at ambient temperature, said hair dye composition being at a temperature ranging from 30° C. to 50° C., applying said hair dye composition to human hair at ambient temperature or at a temperature between 30° C. and 50° C. and permitting said hair dye composition to remain in contact with said hair for a period of time sufficient to dye said hair.

2. The method of claim 1 wherein said aqueous medium contains 1 to 40 weight percent of an organic solvent, said solvent being selected from the group consisting of glycerol, 1-propanol, a $C_4$ alkanol other than tert. butanol, a $C_5$ alkanol, phenyl ethanol, benzyl alcohol, propylene glycol, diethylene glycol, triethylene glycol, tetraethylene glycol, butylene glycol, propylene glycol methyl ether, dipropylene glycol methyl ether, tripropylene glycol methyl ether, ethylene glycol methyl ether, ethylene glycol ethyl ether, ethylene glycol butyl ether, diethylene glycol methyl ether, diethylene glycol ethyl ether, diethylene glycol butyl ether, ethylene glycol phenyl ether, diethylene glycol isobutyl ether, diethylene glycol hexyl ether, trimethylene glycol ethyl ether, trimethylene glycol butyl ether, 1-butoxy-2-propanol, ethylene glycol diethyl ether, ethylene glycol dibutyl ether, ethylene glycol monobenzyl ether, diethylene glycol dimethyl ether, diethylene glycol diethyl ether, diethylene glycol dibutyl ether, triethylene glycol dimethyl ether, tetraethylene glycol dimethyl ether, 1,3-butylene glycol methyl ether and a mixture thereof.

3. The method of claim 1 wherein said nitrobenzene dye is present in said hair dye composition in an amount such that at ambient temperature at least 0.5 percent by weight of said nitrobenzene dye is present in an undissolved state in said hair dye composition.

4. The method of claim 1 wherein said hair dye composition is maintained in contact with said hair at a temperature greater than ambient temperature, said hair being heated with a drying hood or cap.

5. The method of claim 1 wherein the application of said hair dye composition to the hair and the contact of said hair dye composition with the hair are effected at ambient temperature.

6. The method of claim 1 wherein said nitrobenzene dye is selected from the group consisting of
2-N-β-hydroxyethylamino-5-N,N-bis-β-hydroxyethylamino nitrobenzene,
2-N-methylamino-5-N,N-bis-β-hydroxyethylamino nitrobenzene, 2-N-methylamino-5-N-methyl-N-β-hydroxyethylamino nitrobenzene,
2-N-β-hydroxyethylamino-5-N-methyl-N-β-hydroxyethylamino nitrobenzene,
2-N-methylamino-4-β-hydroxyethoxy nitrobenzene,
2-N-β-hydroxyethylamino nitrobenzene,
3-β-hydroxyethoxy-4-N-β-hydroxyethylamino nitrobenzene,
3-methoxy-4-N-β-hydroxyethylamino nitrobenzene,
2-N-β-hydroxyethylamino-5-amino nitrobenzene,
2-amino-5-N-β-hydroxyethylamino nitrobenzene,
3,4-diamino nitrobenzene,
3-amino-4-N-β-hydroxyethylamino nitrobenzene,
2-amino-5-N-methylamino nitrobenzene,
3,4-bis-N-β-hydroxyethylamino nitrobenzene,
3-amino-4-hydroxy nitrobenzene,
2,5-N-β-hydroxyethylamino nitrobenzene,
2-hydroxy-5-amino nitrobenzene,
3-hydroxy-4-amino nitrobenzene,
2-amino-5-hydroxy nitrobenzene,
2-N-β-hydroxyethylamino-5-hydroxy nitrobenzene,
2-amino-3-hydroxy nitrobenzene and
3-hydroxy-4-N-β-hydroxyethylamino nitrobenzene.

7. The method of claim 1 wherein said hair dye composition includes a nitrobenzene dye other than the said nitrobenzene dye defined therein.

8. The method of claim 1 wherein said hair dye composition has a pH ranging from 3 to 11.

9. In a method for dyeing human hair with a hair dye composition comprising in an aqueous medium 0.2 to 20 weight percent of a nitrobenzene dye, the improvement comprising selecting as said nitrobenzene dye one having a value of KC lim greater than 2 in an aqueous medium, said KC lim being defined as the ratio $$KC \lim = \frac{C \lim 50}{C \lim 18},$$

C lim 50 being the limiting concentration of said nitrobenzene dye at 50° C. and C lim 18 being the limiting concentration of said nitrobenzene dye at 18° C., in an aqueous medium, said nitrobenzene dye being selected from the group consisting of
2-N-β-hydroxyethylamino-5-N,N-bis-β-hydroxyethylamino nitrobenzene,
2-N-methylamino-5-N,N-bis-β-hydroxyethylamino nitrobenzene,
2-N-methylamino-5-N-methyl-N-β-hydroxyethylamino nitrobenzene,
2-N-methylamino-4-β-hydroxyethoxy nitrobenzene,
2-N-β-hydroxyethylamino nitrobenzene,
3-methoxy-4-N-β-hydroxyethylamino nitrobenzene,
2-N-β-hydroxyethylamino-5-amino nitrobenzene,
2-amino-5-N-β-hydroxyethylamino nitrobenzene,
3,4-bis-N-β-hydroxyethylamino nitrobenzene,
2,5-N-β-hydroxyethylamino nitrobenzene,
2-amino-5-hydroxy nitrobenzene,
2-N-β-hydroxyethylamino-5-hydroxy nitrobenzene,
2-amino-3-hydroxy nitrobenzene and
3-hydroxy-4-N-β-hydroxyethylamino nitrobenzene,
said nitrobenzene dye being present in said hair dye composition supersaturated relative to its solubility limit at ambient temperature, said hair dye composition being at a temperature ranging from 30° C. to 50° C., applying said hair dye composition to human hair at ambient temperature or at a temperature between 30° C. and 50° C. and permitting said hair dye composition to remain in contact with said hair for a period of time sufficient to dye said hair.

* * * * *